*(12)* United States Patent
Sinha et al.

(10) Patent No.: US 6,294,374 B1
(45) Date of Patent: Sep. 25, 2001

(54) USE OF CATALYTIC ANTIBODIES FOR SYNTHESIZING EPOTHILONE

(75) Inventors: Subhash C. Sinha, San Diego; Richard A. Lerner, La Jolla; Carlos F. Barbas, III, Del Mar, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/415,453

(22) Filed: Oct. 8, 1999

(51) Int. Cl.$^7$ ........................................... C12S 13/00
(52) U.S. Cl. ........................................ 435/280; 435/188.5
(58) Field of Search ................................. 435/280, 188.5

(56) References Cited

U.S. PATENT DOCUMENTS 5,733,757 * 3/1998 Barbas et al. .................... 435/148

OTHER PUBLICATIONS

Barbas, C.F., et al. (1997) Science 278, 2085–2092.*
List, B., et al. (1999) J. Am. Chem. Soc. 121(32), 7283–7291.*
Hoffmann, T., et al. (1998) J. Am. Chem. Soc. 120(12), 2768–2779.*
Shulman, H., et al. (1999) Bioorg. Med. Chem. Lett. 9, 1745–1750.*
Sinha, S. C., et al. (1998) Proc. Natl. Acad. Sci, USA 95, 14603–14608.*
Schultz, et al., "From Molecular Diversity to Catalysis: Lessons from the Immune System", *Science* 269: 1835–1842 (1995).
Wagner, et al., "Efficient Aldolase Catalytic Antibodies That Use the Enamine Mechanism of Natural Enzymes", *Science* 270: 1797–1800 (1995).
Keinan, et al., "The First Decade of Antibody Catalysis: Perspective and Prospects", *Israel J. Chem.* 36: 113–119 (1996).
Zhong, et al., "Antibody–Catalyzed Enantioselective Robinson Annulation", *J. Am. Chem. Soc.* 119: 8131–8132 (1997).
List, et al., "Enantioselective Total Synthesis of Some Brevicomins Using Aldolase Antibody 38C2", *Chem. Eur. J.* 4: 881–885 (1998).
Zhong, et al., "Catalytic Enantioselective Retro–Aldol Reactions: Kinetic Resolution of β–Hydroxyketones with Aldolase Antibodies", *Angew. Chem. Int. Ed. Engl.* 37: 2481–2484 (1998).
Reymond, "Catalytic Antibodies for Organic Synthesis", *Top. Curr. Chem.* 200: 59–93 (1999).

* cited by examiner

*Primary Examiner*—Charles L. Patterson, Jr.
(74) *Attorney, Agent, or Firm*—Donald G. Lewis

(57) ABSTRACT

Three monoclonal aldolase antibodies, generated against a β-diketone hapten by reactive immunization, catalyzed rapid and highly enantioselective retro-aldol reactions providing ent-9a–k by kinetic resolution. Compounds 9a, 9g and 9k were resolved in multi-gram quantities using 0.005–0.0004 mol % antibody catalyst. Enantiomerically pure starting materials, 9a–k, are useful synthons for the construction of epothilones A–E (2–6) and their analogs including 13-alkyl derivatives. Previously, the use of compound 9a as a synthon was reported in the preparation of epothilones A–D, 2–5. To further expand this synthon-based strategy, syntheses of epothilone E, 6, 13-methyl epothilone C, 7, and their trans-isomers have been achieved starting from enantiomerically pure thiazole aldols 9g and 9a, respectively, prepared by large-scale antibody catalyzed resolutions.

3 Claims, 4 Drawing Sheets

$R_1$ = Me, CH$_2$OH, SMe, OMe
R = Me, Et, n-Pr, n-Bu, n-Pentyl, n-But-1-en-4-yl

| entry | compounds | 84G3 ee | 85H6 ee | 93F3 ee |
|---|---|---|---|---|
| 1 | 9a: R= $R_1$= Me | 98 (50)[a] | 94 (50)[a] | 98 (50)[a] |
| 2 | 9b: R= Et, $R_1$= Me | 99 (51) | 99 (50) | 99 (50) |
| 3 | 9c: R= Pr, $R_1$= Me | 99 (50) | 99 (50) | 99 (50) |
| 4 | 9d: R= Bu, $R_1$= Me | 99 (50) | 99 (50) | 99 (50) |
| 5 | 9e: R= Pen, $R_1$= Me | 97 (52) | 97 (55) | 97 (53) |
| 6 | 9f: R= But-1-ene, $R_1$= Me | 98 (52) | 98 (50) | 99 (50) |
| 7 | 9g: R= Me, $R_1$= $CH_2OH$ | 99 (50) | 99 (50) | 99 (50) |
| 8 | 9h: R= $CH_2F$, $R_1$= Me | 96 (54) | 99 (55) | 98 (52) |
| 9 | 9i: R= Me, $R_1$= OMe | >95[b] (51) | >95[b] (52) | >95[b] (52) |
| 10 | 9j: R= Me, $R_1$= SMe | 99 (53) | 99 (50) | 99 (54) |
| 11 | 9k: R= Et, $R_1$= SMe | 99 (50) | 99 (50) | 99 (52) |

USE OF CATALYTIC ANTIBODIES FOR SYNTHESIZING EPOTHILONE

FIELD OF INVENTION

The invention relates to catalytic antibodies having aldolase activity. More particularly the invention relates to a process for enantioselectively purifying a racemic mixture of aldol synthons by means of an antibody catalyzed retro-aldol reaction.

BACKGROUND

Reactive immunization provides a unique opportunity to generate catalytic antibodies that are efficient yet broad in scope (Shultz, P. G., et al., *Science* 1995, 269, 1835; Keinan, E., et al. *Israel J. Chem.* 1996, 36, 113; and Reymond, J.-L. *Top. Curr. Chem.* 1999, 200, 59). Recently, two aldolase antibodies 33F12 and 38C2 were generated against a β-diketone hapten, 6-(4-glutaramidophenyl)-hexane-2,4-dione, using reactive immunization (Wagner, J., et al., *Science* 1995, 270, 1797). These antibody catalysts were found to be useful synthetic catalysts in that they catalyze a wide range of aldol- and retro-aldol reactions, typically with a very high degree of enantioselectivity (Zhong, G., et al.,*J. Am. Chem. Soc.* 1997, 119, 8131; List, B., et al., *Chem. Eur. J.* 1998, 4, 881; Hoffmann, T., et al.,*J. Am. Chem. Soc.* 1998, 120, 2768; Barbas, C. F, et al., *Science* 1998, 278, 2085; Zhong, G., et al. *Angew. Chem. Int. Ed. Engl.* 1998, 37, 2481; and List, B., et al., *J. Am. Chem. Soc.* 1999, 121, 7283).

Epothilones A–E, 2–6, are sixteen-membered macrolides isolated from myxobacteria, i.e., *Sorangium cellulosum* strain 90 (Bollag, D. M., et al., *Cancer Res.* 1995, 55, 2325; Gerth, K., et al.,*J. Antibiot.* 1996, 49, 560; Hofle, G., et al., *Angew. Chem. Int. Ed. Engl.* 1996, 35, 1567; and Nicolaou, K. C., et al., *Angew. Chem. Int. Ed. Engl.* 1998, 37, 2014). Several total syntheses of epothilones A–E as well as their analogs have been achieved. For the first total syntheses of epothilones A–D, see: (a) Balog, A., et al.,*Angew. Chem. Int. Ed. Engl.* 1996, 35, 2801; Su, D.-S., et al.,*Angew. Chem. Int. Ed. Eng.* 1997, 36, 757. Syntheses of epothilones A and C were simultaneously reported by Nicolaou and Schinzer groups (Schinzer, D., et al., *Angew. Chem. Int. Ed. Engl.* 1997, 36, 523; and Nicolaou, K. C., et al.,*Angew. Chem. Int. Ed. Eng.* 1997, 36, 525). For the synthesis of epothilone E, see: Nicolaou, K. C., et al., *Angew. Chem. Int. Edn. Eng.* 1998, 37, 84. For the recent total synthesis of other epothilones see: May, S. A., et al., *Chem. Commun.* 1998, 1597; Mulzer, J., et al. *Tetrahedron Lett.* 1998, 39, 8633; Harris, C. R., et al. *Tetrahedron Lett.* 1999, 40, 2263; Nicolaou, K. C., et al., *Chem. Commun.* 1999, 519; Nicolaou, K. C., et al., *Bioorg. Med. Chem.* 1999, 7, 665; and White, J. D., et al., *J. Org. Chem.* 1999, 64, 684. The biological properties of epothilones A–E and their analogs have also been recorded (Chou, T.-C., et al., *Proc. Natl. Acad. Sci. USA* 1998, 95, 9642 and references cited therein). Recently, a synthesis of the naturally occurring epothilones A–D, 2 and 4, starting from aldol products obtained either by an antibody 38C2-catalyzed aldol addition of acetone to the aldehyde 10 or by an enantioselective resolution of a racemic aldol product using antibody 38C2 (Sinha, S. C., et al., *Proc. Natl. Acad. Sci. USA* 1998, 95, 14603).

SUMMARY

It is disclosed herein that catalytic antibodies 84G3, 85H6 and 93F3 have antipodal reactivity with regard to catalytic antibody 38C2 and that these antibodies are effective with regard to the catalytic resolution of the thiazole aldols 9a–k on a preparative scale. It is further disclosed that this antibody-based synthon approach provides an attractive synthetic route to natural epothilones and their 13-alkyl derivatives as exemplified here with syntheses of epothilone E, 6, 13-alkyl epothilone C, 7 and their trans isomers.

Catalytic antibodies 84G3, 85H6 and 93F3 were generated against hapten 1 and have been deposited with the ATCC. Like 33F12 and 38C2, these antibodies also catalyze aldol reactions with a wide variety of aldehydes and ketones via an enamine mechanism. However, the aldol products prepared with these new antibodies are antipodal as compared to those obtained by catalysis with the antibodies 33F12 and 38C2. Two of the new catalysts, 84G3 and 93F3, operate with the highest catalytic proficiencies yet observed with antibodies, $(k_{cat}/K_m)k_{un} > 10^{13}$ M$^{-1}$. These new catalysts present significant advantages with regard to the synthesis of epothilones and their analogs.

One aspect of the invention is directed to a process for enantioselectively resolving a racemic mixture of an aldol synthon. The racemic mixture includes a first and a second enantiomer of the aldol synthon. The racemic mixture need not be a 50/50 mixture of the two enantiomers. In the first step of the process, the first enantiomer of the aldol synthon is enantioselectively converted to form an aldehyde product by means of a retro-aldol reaction catalyzed by a catalytic antibody. The second enantiomer of the aldol synthon is left unmodified in this process. The aldehyde product is then separated from the unmodified second aldol synthon to achieve an enantioselective resolution of the aldol synthon. Preferred catalytic antibodies include 84G3, 85H6, and 93F3. In a preferred mode, the synthons and the retro-aldol reaction are represented as follows:

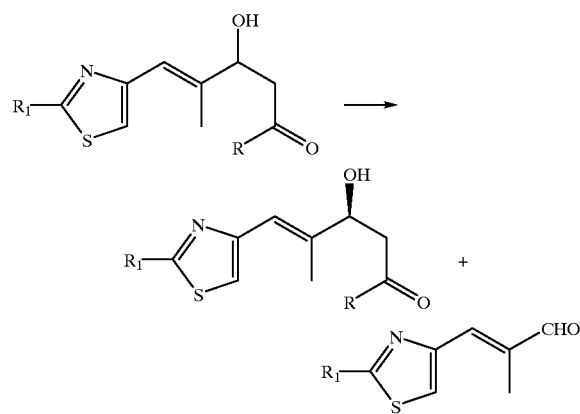

Preferred substituents for $R_1$ include Me, CH$_2$OH, SMe, and OMe. Preferred substituents for R include Me, Et, n-Pr, n-Bu, n-Pentyl, and n-Bu-1-en-4-yl.

DETAILED DESCRIPTION

Figure 1:
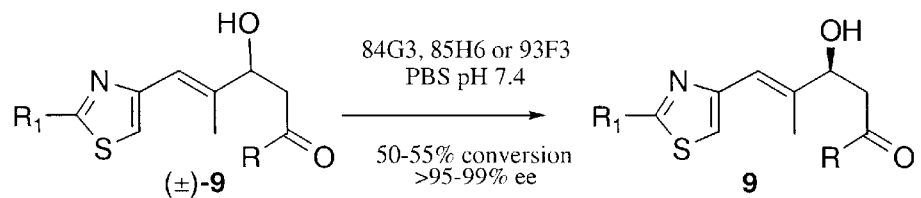
FIG. 1 illustrates a kinetic resolution of compound (±)-9 by an antibody catalyzed retro-aldol reaction using catalytic antibodies 84G3, 85H6 and 93F3.
Figure 2:
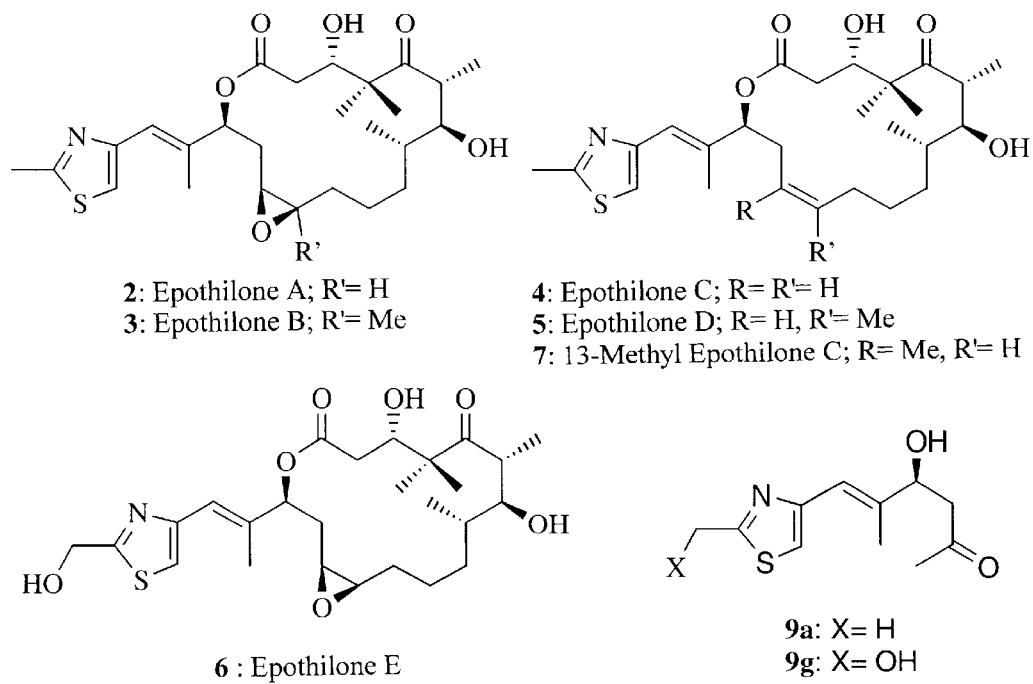
FIG. 2 illustrates structures of epothilones A–E, 2–6, 13-methyl epothilone C, 7, and an antibody 38C2 resolved aldol starting material 9.
Figure 3:
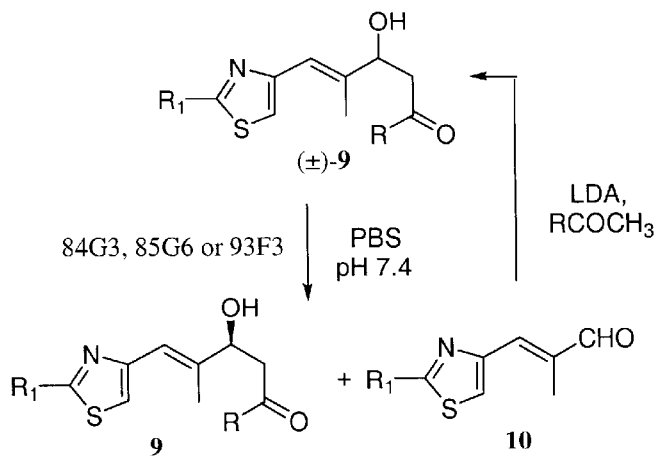
FIG. 3 tabulates the enantiomeric efficiencies of the kinetic resolution of compounds (±)-9a–k by an antibody catalyzed retro-aldol reaction using catalytic antibody 84G3, 85H6 or 93F3. (a.) Numbers in the parentheses represent percent conversion. (b.) Peaks of the two enantiomers on HPLC trace were not base-line separable.
Figure 4:
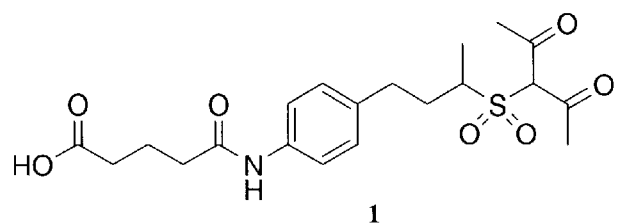
FIG. 4 illustrates the hapten employed for generating catalytic antibodies 84G3, 85H6 and 93F3.

Disclosed herein is the resolution of compound 9a and its analogs, 9b–k, using antibodies 84G3, 85H6 or 93F3. Compounds 9a, 9g and 9k have been resolved in multi-gram quantities using 0.003, 0.005 and 0.0004 mol %, respectively, of antibody 84G3. Also disclosed is the syntheses of epothilone E, 6, and 13-methyl epothilone C, 7, starting from synthons 9g and 9a, respectively.

Deposit of Hybridomas

Deposits for hybridoma 84G3, having ATCC accession number PTA-824, for hybridoma 85H6, having ATCC accession number PTA-825, and for hybridoma 93F3, having ATCC accession number PTA-823 were made in compliance with the Budapest Treaty requirements that the duration of the deposits should be for 30 years from the date of deposit at the depository or for the enforceable life of a U.S. patent that matures from this application, whichever is longer. The hybridoma cell lines will be replenished should any of them become non-viable at the depository, under the terms of the Budapest Treaty, which assures permanent and unrestricted availability of the progeny of the hybridomas to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the hybridoma deposit should die or be lost or destroyed when cultivated under suitable conditions, it will be promptly replaced on notification with a viable specimen of the same hybridoma. Availability of the deposit is not to be construed as a license to practice the invention in contravention of the rights granted under the authority of any government in accordance with its patent laws.

Kinetic Resolution

Catalysis of the retro-aldol reaction of compound (±)-9a is performed with the above three indicated catalytic aldolase antibodies, raised against the hapten 1. It is disclosed that antibodies, 84G3, 85H6 and 93F3, efficiently catalyzed the retro-aldol reaction of (±)-9a to aldehyde 10a and acetone. The kinetic resolution of compound (±)-9a by antibody catalyzed retro-aldol reaction was studied using chiral reverse phase HPLC. It is also disclosed that, when the reactions reached ~50% conversion, the remaining aldols could be isolated in essentially enantiomerically pure form. A solution (100 ml) of compound (±)-9a (0.01 M, 10 ml) and antibody 84G3 (6 mM, 90 ml in PBS buffer, pH 7.4) was kept at room temperature under argon atmosphere for 12 h. The reaction mixture was then shown to contain only one enantiomer of (±)-9a by HPLC analysis equipped with a chiral reverse phase column. The unreacted aldol compound was identified as 9a by comparison with the synthetic sample of 9a as well as one derived from the resolution of (±)-9a with the antibody 38C2. Using the methodology of Patterson (Paterson, I., et al., *Tetrahedron* 1990, 46, 4663.), a sample of 9a for comparison was prepared by the reaction of prop-1-en-2-ol diisocamphenylborinate (prepared from (+)-(Ipc)$_2$BOTf and acetone) with the aldehyde 9a. The HPLC conditions are indicated infra.

Based on these results, several analogs of (±)-9a were prepared and the relative rates of their reaction with these antibodies and the enantiomeric purity of the remaining unreacted aldols were determined. Compounds (±)-9a–k ($10^{-2}$ M solution in $CH_3CN$, 10 ml) were incubated with the antibody 84G3, 85H6 or 93G3 (90 ml of 6 mM antibody solution in PBS buffer, pH 7.4) and progress of the reaction was followed by HPLC equipped with a chiral reverse phase ODR column (Daicel Chemical Industries). The HPLC conditions are indicated infra. It is disclosed that compounds, 9b–k, could also be obtained with very high enantiomeric purity at 50% conversion by kinetic resolution of (±)-9b–k with the antibodies 84G3, 85H6 or 93F3 (Table 1). All three catalysts gave similar results with antibodies 84G3 and 93F3 demonstrating a rate enhancement slightly greater than that observed with 85H6. Increasing the chain length from methyl in 9a to ethyl and propyl group in 9b and 9c, respectively, also increased the relative rate of reaction. Further increases in the chain length to butyl and pentyl groups as in compounds 9d and 9e decreased the rate. Substrates with a $C_5$-chain length were very slow and the catalysts did not tolerate further extension at this position. Nevertheless, the resolved products 9a–k were obtained with very high enantiomeric purity at 50–54% conversion. Interestingly, compound 9k was the fastest reacting substrate with all of the antibodies, and could be resolved with >99% enantioselectivity in less than 10 min employing 0.5 mol % antibody 93F3. When the catalyst concentration was reduced to 0.01 mol %, the reaction was complete after overnight incubation.

The feasibility of resolving compound (±)-9a and its analogs with these antibodies on a synthetically useful scale was also characterized. Antibody 84G3 was used to perform the resolution of compounds (±)-9a, (±)-9g and (±)-9k. Compound (±)-9a (16.8 g, 74.7 mmol) was incubated with 0.003 mole percent of antibody 84G3 (340 mg, 0.00227 mmol) in PBS buffer (pH 7.4) at 37° C. (See: Supporting Information). Progress of the reaction was followed by disappearance of the peak corresponding to ent-9a in the HPLC trace. In this way, the racemic mixture was resolved in seven days affording 9a with greater than 95% enantiomeric purity in 45% isolated yield. Aldehyde 10a was recovered in 42% isolated yield and converted back to the racemic aldol for subsequent recycling. Antibodies recovered after one reaction cycle retained their catalytic activity. Thus, even though the process is a kinetic resolution the overall yield could be enhanced because the products could be recycled.

Similarly, compound (±)-9g (1.45 g, 6.02 mmol) was resolved using 0.005 mole percent of antibody 84G3 (45 mg, 0.0003 mmol) with an overall turnover number of more than 10,000 to afford enantiomerically pure 9g (0.7 g, 48%) and aldehyde 10 g (516 mg, 47%) respectively (See: Supporting information). The fastest substrate in this series, (±)-9k (8.4 g, 31 mmol), was resolved with as little as 0.0004 mol % of the antibody 84G3 (20 mg, 0.000133 mmol) in a week to afford 9k in 49% and the corresponding aldehyde 10k in 45% isolated yields (See: Supporting information).

Synthesis of epothilone E, 6

Figure 5:
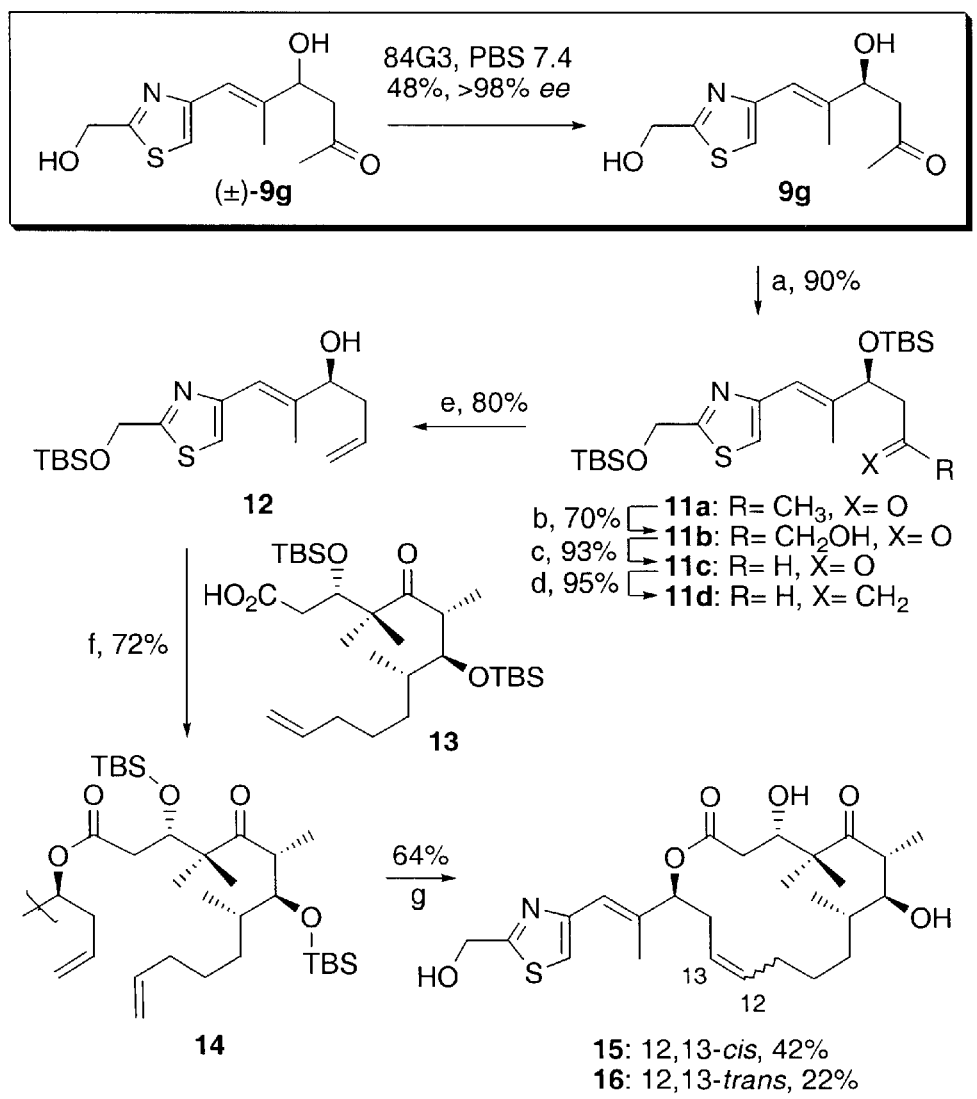
FIG. 5 illustrates the total synthesis of desoxy epothilone E (15) leading to a formal synthesis of epothilone E (6). Key: (a) TBSCl, imidazole, DMF at room temperature for 16 hours; (b) i. TMSOTf, lutidine, $CH_2Cl_2$, −78° C., 3 hours, ii. $CF_3C(O)Me$, oxone, acetonitrile, 0° C., 1 hour; (c) i. $NaBH_4$, MeOH, 0° C., 0.5 hour, ii. $Pb(OAc)_4$, benzene, from 0° C. to room temperature over 1 hour; (d) $MePPh_3I$, BuLi, THF, 0° C., 0.5 hour; (e) i. TBAF, THF, 0° C., 2 hours, ii. TBSCl, i-$Pr_2EtN$, $CH_2Cl_2$, at room temperature for 16 hours; (f) EDC, $CH_2Cl_2$, from 0° C. to room temperature over 12 hours; (g) i. Grubb's catalyst, $CH_2Cl_2$, at room temperature for 16 hours, ii. HF-pyridine, THF, from 0 to room temperature for 12 hours.

Compounds 9a–k are useful synthons for the construction of the naturally occurring epothilones 2–6 as well as their analogs modified in the thiazole ring. Compounds with a methyl ketone function, such as in 9a, were converted in a sequence of five simple and high yielding steps to the key alkene or iodoalkene precursors used in the syntheses of epothilones A–D, 2–5, by metathesis and/or macrolactonization approaches (Sinha, S. C., et al., *Proc. Natl. Acad. Sci. USA* 1998, 95, 14603). A similar strategy was used to synthesize epothilone E, 6, starting from the compound 9g by the metathesis approach (FIG. 5).

Compound 9g, isolated from the antibody reaction was first protected as the bis-TBS ether to give 11a. The methyl ketone functionality of compound 11a was converted to its TMS-enol ether with TMSOTf and lutidine at −78° C., and then reacted with $CF_3COCH_3$/oxone to yield the primary hydroxy ketone 11b. Compound 11b was reduced to the corresponding vicinal diol, which was then cleaved with $Pb(OAc)_4$ to provide the aldehyde 11c. Wittig reaction of aldehyde 11c with methylphosphorane afforded the allylic alcohol 11d. Both the TBS groups of compound 11d were removed by reaction with TBAF and subsequently the primary alcohol was selectively protected as the TBS ether to yield the compound 12.

Compound 12 was esterified with acid 13 providing ester 14 (Sinha, S. C., et al., *Proc. Natl. Acad. Sci. USA* 1998, 95, 14603). Metathesis of compound 14 with Grubb's catalyst yielded the cyclized product along with its trans isomer in a ratio of 3:2. Subsequent deprotection yielded compound 15 and its trans-isomer, 16. The spectral data ($^1$H NMR, $^{13}$C NMR, MS, optical rotation) of 15 were identical to the published data. Conversion of 15 to epothilone E, 6, has been reported (Nicolaou, K. C., et al., *Angew. Chem. Int. Ed. Eng.* 1998, 37, 84).

Physical Data for Compound 13

$[\alpha]_D$=−13.42° (c=0.37, $CHCl_3$); $^1$H NMR (400 MHz, $CDCl_3$): δ7.01 (s, 1H), 6.52 (s, 1H), 5.80 (m, 1H), 5.12 (d, J=17.4 Hz, 1H), 5.09 (d, J=11.3 Hz, 1H), 4.93 (s, 2H), 4.18 (t, J=6.7 Hz, 1H), 2.38 (m, 3H), 2.02 (s, 3H), 0.93 (s, 9H), 0.11 (s, 6H); $^{13}$C NMR (100 MHz, $CDCl_3$): δ172.1, 153.0, 141.4, 134.6, 119.0, 117.8, 115.7, 76.4, 63.2, 40.0, 25.7, 18.2, 14.4, −5.5; MS: 340 (MH$^+$), 362 (MNa$^+$).

Physical Data for Compound 14

$[\alpha]_D$−43.7°(c=0.3, $CHCl_3$), Lit. −44.2°(c=0.6, $CHCl_3$)

Synthesis of 13-methyl epothilone C, 7 and its trans isomer, 27

Figure 6:
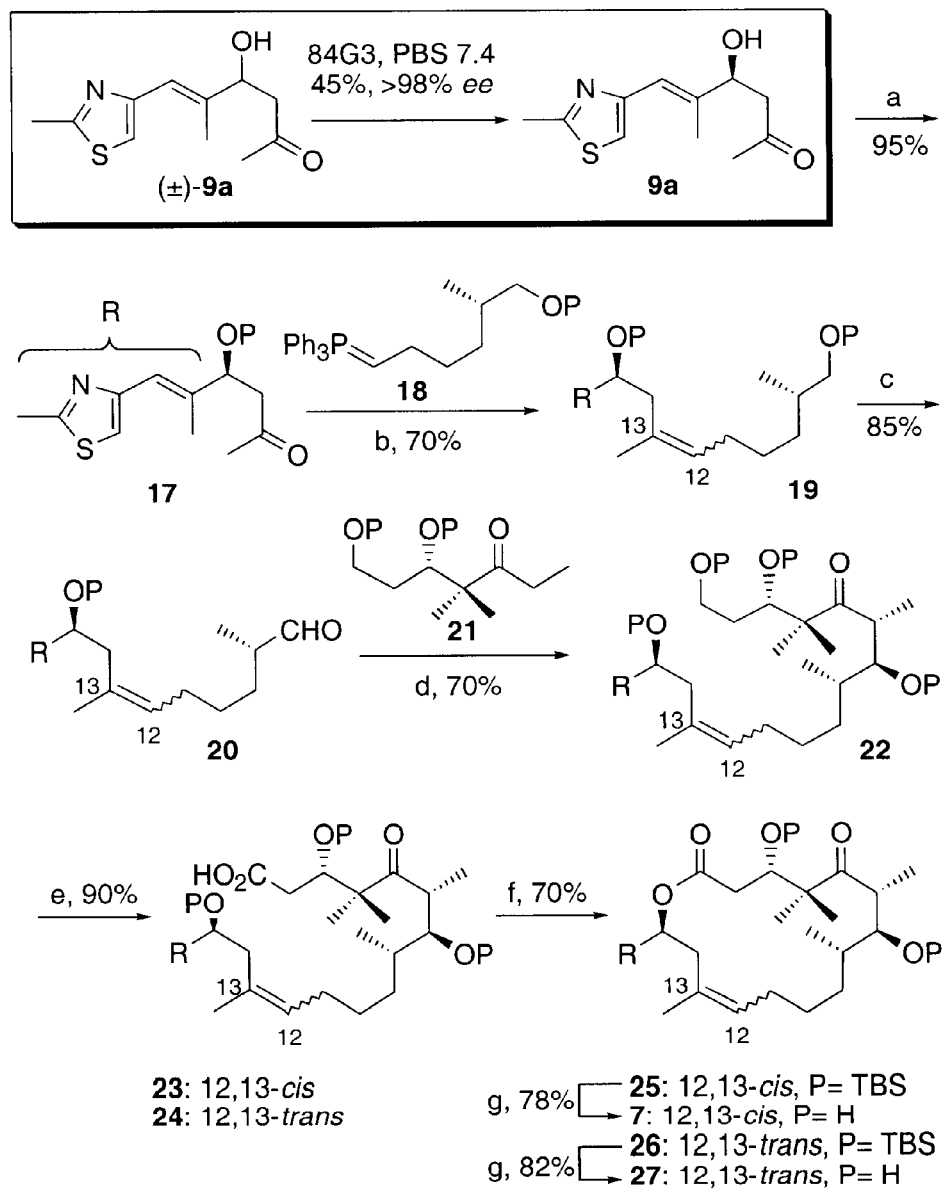
FIG. 6 illustrates the total synthesis of 13-methyl epothilone C, 7. (P=tert-butyldimethylsilyl), Key: (a) TBSCl, imidazole, DMF, at room temperature for 16 hours; (b) 18, BuLi, ether, at room temperature for 1 hour; (c) i. TsOH, MeOH—$CH_2Cl_2$, 0° C., 0.5 hour, ii. Dess Martin reagent, $CH_2Cl_2$, at room temperature for 2 hours; (d) i. 21, LDA, THF, −78° C.—−30° C., 2 hours, ii. TBSOTf, lutidine, $CH_2Cl_2$, −78° C.–0° C., 4 hour; (e) i. TsOH, MeOH—$CH_2Cl_2$, 0° C., 0.5 h, ii. Dess Martin reagent, $CH_2Cl_2$, at room temperature for 2 hours, iii. $NaClO_2$, 2-methyl-2-butene, $NaH_2PO_3$, tert-BuOH, $H_2O$, at room temperature for 1 hour; iv. Separation by column chromatography, silica gel, hexane-EtOAc; (f) i. TBAF, THF, rt, 16 h, ii. 2,4,6-trichlorobenzoyl chloride, $Et_3N$, THF, 0° C., 1 hour then slow addition to dilute solution of DMAP, in toluene, 75° C., 3 hours; (g) HF-pyridine, THF, from 0° C. to room temperature over 12 hours.

Compounds 9a–k possess an alkyl ketone in their structure and thus they are especially valuable for the preparation of 13-alkyl analogs of the aforementioned epothilones. This strategy is exemplified by a synthesis of 13-methyl epothilone C, 7, and its trans isomer, 27 (FIG. 6). Compound 9a was silylated as above to afford 17. Wittig reaction of the latter compound with a known Wittig salt 18 afforded 19 as a mixture (55:45) of E and Z olefins (Nicolaou, K. C., et al., *J. Am. Chem. Soc.* 1997, 119, 7974). This mixture was taken to the next step without separation. The primary alcohol in 19 was unmasked by deprotection and then oxidized to afford aldehyde 20. An aldol reaction of the latter aldehyde with the known ketone 22 was carried out using LDA as a base (Claus, E., et al., *Tetrahedron Lett.* 1997, 38, 1359). The free hydroxy group in the aldol products were then protected as TBS ethers affording 22 as the major isomer contaminated with 6,7-bisepi-22. The primary alcohol in the mixture of 22 and 6,7-bisepi-22 was then selectively deprotected and oxidized in two steps via the aldehyde to the corresponding acids. Compounds 23 and 24 were then isolated by chromotography. Selective deprotection of the TBS ether at C-15 in 23 and 24 followed by lactonization under Yamaguchi conditions afforded the corresponding lactones 25 and 26, which were then deprotected with HF-pyridine providing 7 and its trans isomer, 27.

Supporting Information

HPLC conditions for compounds 8a–k: $\lambda_{max}$=254 nm; reverse phase ODR column, Daicel Chemical Industries. Solvent systems: acetonitrile:water (3:17, System A; 1:4, System B; 1:3, System C; 3:7, System D and 2:3, System E) and 0.1% TFA at a flow rate of 0.4 ml/min.

Compound 8a

Antibody 84G3 (12.5 mg/ml, 27.2 ml, 0.34 g, 0.00227 mmol) was added to a degassed solution of the compound (±)-8a (16.8 g, 75 mmol) in PBS buffer (1.55 l, pH 7.4) and $CH_3CN$ (40 ml), and the mixture was incubated under argon atmosphere at 37° C. for 5 days. At more than 98% consumption of one enantiomer as judged by HPLC analysis, the mixture was filtered using amicon to recover the antibody. The filtrate was passed through a reverse phase column (C-18) to elute first water and then the compounds were isolated using methanol as eluants. The solvents were removed and the residue was purified over silica gel (hexane-ethyl acetate, 9:1–4:1) to afford compounds 8a (7.6 g, 45%) and the aldehyde 9a (5.29 g, 42%).

Retention time ($R_t$) of 8a, 13.87 min and ent-8a, 15.28 min (solvent system A). Physical data of 8a: $[\alpha]_D$−34.3° (c=1.62, $CHCl_3$); $^1$H NMR (600 MHz, $CDCl_3$): δ6.89 (s, 1H), 6.55 (s, 1H), 4.58 (dd, J=9.3, 2.2 Hz, 1H), 3.72 (br s, 1H), 2.72 (dd, J=16.7, 9.4 Hz, 1H), 2.66 (s, 3H), 2.64 (dd, J=16.7, 3.0 Hz, 1H), 2.18 (s, 3H), 1.98 (s, 3H); $^{13}$C NMR (150.9 MHz, $CDCl_3$): δ208.9, 164.7, 152.5, 140.5, 118.6, 115.7, 72.6, 48.7, 30.9, 19.0, 14.7; MS (FAB): 226 (MH$^+$), 248 (MNa$^+$).

Compound 8b $R_t$ of 8b, 27.07 min and ent-8b, 30.72 min (solvent system A). Physical data of 8b: $^1$H NMR (400 MHz, $CDCl_3$): δ6.90 (s, 1H), 6.56 (s, 1H), 4.59 (dd, J=8.6, 3.5 Hz, 1H), 3.42 (br, 1H), 2.67 (s, 3H), 2.67 (m, 2H), 2.47 (q, J=7.3 Hz, 2H), 2.00 (s, 3H), 1.04 (t, J=7.3 Hz, 3H); $^{13}$C NMR (100.6 MHz, $CDCl_3$): δ211.6, 164.8, 152.6, 140.7, 118.6, 115.7, 72.8, 47.5, 37.0, 19.1, 14.7, 7.5; MS: 240 (MH$^+$), 262 (MNa$^+$).

Compound 8c $R_t$ of 8c, 15.48 min and ent-8c, 17.18 min (solvent system D). Physical data of 8c: $^1$H NMR (400 MHz, $CDCl_3$): δ6.91

(s, 1H), 6.55 (s, 1H), 4.58 (dd, J=7.8, 4.4 Hz, 1H), 3.20 (br, 1H), 2.67 (s, 3H), 2.67 (m, 2H), 2.42 (t, J=7.3 Hz, 2H), 2.01 (s, 3H), 1.59 (m, 2H), 0.89 (t, J=7.4 Hz, 3H); $^{13}$C NMR (100.6 MHz, CDCl$_3$): δ211.6, 164.7, 152.6, 140.4, 118.7, 115.8, 72.8, 47.7, 45.7, 19.1, 17.0, 14.8, 13.7; MS: 254 (MH$^+$), 276 (MNa$^+$).

Compound 8d

R$_t$ of 8d, 15.87 min and ent-8d, 17.34 min (solvent system E). Physical data of 8d: $^1$H NMR (400 MHz, CDCl$_3$): δ6.90 (s, 1H), 6.55 (s, 1H), 4.58 (m, 1H), 3.40 (s, 1H), 2.67 (s, 3H), 2.67 (m, 2H), 2.44 (t, J=7.3 Hz, 2H), 2.00 (s, 3H), 1.53 (m, 2H), 1.28 (m, 2H), 0.87 (t, J=7.3 Hz, 3H); $^{13}$C NMR (100.6 MHz, CDCl$_3$): δ211.6, 164.6, 152.7, 140.3, 118.7, 115.8, 72.8, 47.7, 43.5, 25.6, 22.2, 19.1, 14.7, 13.8; MS: 268 (MH$^+$), 290 (MNa$^+$).

Compound 8e

R$_t$ of 8e, 23.86 min and ent-8e, 26.56 min (solvent system E). Physical data of 8e: $^1$H NMR (400 MHz, CDCl$_3$): δ6.88 (s, 1H), 6.54 (s, 1H), 4.57 (d, J=8.9 Hz, 1H), 3.71 (d, J=2.8 Hz, 1H), 2.65 (s, 3H), 2.65 (m, 2H), 2.44 (t, J=7.6 Hz, 2H), 1.98 (s, 3H), 1.54 (m, 2H), 1.24 (m, 4H), 0.83 (t, J=7.2 Hz, 3H); $^{13}$C NMR (100.6 MHz, CDCl$_3$): δ211.4, 164.7, 152.6, 140.6, 118.6, 115.7, 72.8, 47.8, 43.8, 31.3, 23.2, 22.4, 19.1, 14.8, 13.9; MS: 282 (MH$^+$), 304 (MNa$^+$).

Compound 8f

R$_t$ of 8f, 20.12 min and ent-8f, 22.51 min (solvent system D). Physical data of 8f: $^1$H NMR (600 MHz, CDCl$_3$): δ6.91 (s, 1H), 6.56 (s, 1H), 5.77 (m, 1H), 4.98 (m, 2H), 4.60 (d, J=8.5 Hz, 1H), 3.42 (br s, 1H), 2.68 (s, 3H), 2.68 (m, 2H), 2.56 (t, J=7.1 Hz, 2H), 2.31 (m, 2H), 2.01 (s, 3H); $^{13}$C NMR (150.9 MHz, CDCl$_3$): δ211.6, 165.6, 153.5, 141.3, 137.7, 119.6, 117.1, 116.3, 73.7, 48.8, 43.7, 28.3, 20.0, 15.6; MS: 266 (MH$^+$), 288 (MNa$^+$).

Compound 8g

Compound (±)-8g (1.45 g, 6.0 mmol) in acetonitrile (4 ml) was incubated with the antibody 84G3 (12.5 mg/ml, 3.6 ml, 45 mg, 0.0003 mmol) in PBS (pH 7.4, 90 ml) buffer under argon atmosphere for 96 h at 37° C. At more than 98% consumption of one enantiomer as judged by HPLC analysis, the mixture was filtered using amicon to recover the antibody. The filtrate was passed through a reverse phase column (C-18) to elute first water and then the compounds were isolated using methanol as eluants. Solvents were evaporated and the residue was purified over silica gel to afford compounds 8g (0.69 g, 48%, >98% ee) and 9g (0.44 g, 40%).

R$_t$ of 8g, 12.56 min and ent-8g, 14.38 min (solvent system B). Physical data of 8g: [α]$_D$–26.7° (c=0.9, CHCl$_3$); H NMR (500 MHz, CDCl$_3$): δ7.07(s, 1H), 6.58 (s, 1H), 4.92 (s, 2H), 4.60 (m, 1H), 3.32 (br, 1H), 3.01 (br, 1H), 2.73 (m, 2H), 2.22 (s, 3H), 2.03 (s,3H); $^{13}$C NMR (125.75 MHz, CDCl$_3$): δ209.2, 170.0, 152.8, 140.8, 118.5, 116.4, 72.6, 62.0, 48.6, 30.9, 14.8; MS: 264 (MNa$^+$).

Compound 8h

R$_t$ of 8h, 19.68 min and ent-8h, 21.11 min (solvent system A). Physical data of 8h: $^1$H NMR (600 MHz, CDCl$_3$): δ6.93 (s, 1H), 6.60 (s, 1H), 4.93 (dd, J=25.2, 16.4 Hz, 1H), 4.83 (dd, J=25.2, 16.4 Hz, 1H), 4.63 (dd, J=9.4, 2.1 Hz, 1H), 3.86 (br s, 1H), 2.81 (m, 1H), 2.68 (m, 1H), 2.66 (s, 3H), 1.99 (s, 3H); $^{13}$C NMR (150.9 MHz, CDCl$_3$): δ206.0 (d), 165.1, 152.3, 140.6, 118.8, 115.9, 85.3 (d), 72.3, 43.9, 19.0, 14.7.

Compound 8i

R$_t$ of 8i, 35.15 min and ent-8i, 36.14 min (solvent system C). Physical data of 8i: $^1$H NMR (400 MHz, CDCl$_3$): δ6.46 (s, 1H), 6.34 (s, 1H), 4.57 (t, J=5.8 Hz, 1H), 4.06 (s, 3H), 3.01 (br s, 1H), 2.71 (d, J=1.0 Hz, 1H), 2.70 (s, 1H), 2.20 (s, 3H), 2.07 (d, J=1.1 Hz, 3H); $^{13}$C NMR (100.6 MHz, CDCl$_3$): δ209.2, 173.8, 147.3, 139.4, 118.8, 109.3, 72.9, 58.3, 48.6, 30.9, 14.5; MS: 264 (MNa$^+$).

Compound 8j

R$_t$ of 8j, 21.43 min and ent-8j, 20.66 min (solvent system D). Physical data of 8j: [α]$_D$=−35.2° (c=2.05, CHCl$_3$); $^1$H NMR (400 MHz, CDCl$_3$): δ6.93 (s, 1H), 6.50 (s, 1H), 4.58 (m, 1H), 3.14 (d, J=3.0 Hz, 1H), 2.70 (d, J=6.1 Hz, 2H), 2.67 (s, 3H), 2.20 (s, 3H), 2.06 (d, J=1.2 Hz, 3H); $^{13}$C NMR (100.6 MHz, CDCl$_3$): δ209.2, 165.1, 153.3, 140.3, 118.1, 115.8, 72.8, 48.6, 30.9, 16.6, 14.8; MS: 258 (MH$^+$), 280 (MNa$^+$).

Compound 8k

Antibody 84G3 (12.5 mg/ml, 1.6 ml, 0.02 g, 0.000133 mmol) was added to a degassed solution of the compound (±)-8k (5 g, 18.5 mmol) in PBS buffer (450 ml, pH 7.4) and CH$_3$CN (40 ml), and the mixture was incubated under argon atmosphere for 3 days at 37° C. An additional amount of (±)-8k (3.4 g, 12.5 mmol) in a degassed mixture of PBS buffer (300 ml, pH 7.4) and CH$_3$CN (10 ml) was added and the mixture was incubated under argon atmosphere for another 7 days at the same temperature. At more than 98% consumption of one enantiomer as judged by HPLC analysis, the mixture was first centrifuged. The residue was kept aside and the filtrate was passed through a reverse phase column (C-18) to elute first water and then the compounds were isolated using methanol as eluants. The solvents were removed and the combined residue was purified over silica gel (hexane-ethyl acetate, 9:1–4:1) to afford compounds 8k (4.1 g, 49%) and the aldehyde 9k (2.7 g, 41%).

R$_t$ of 8k, 33.20 min and ent-8k, 31.02 min (solvent system E). Physical data of 8k: [α]$_D$=−35.6° (c=0.92, CHCl$_3$); $^1$H NMR (400 MHz, CDCl$_3$): δ6.94 (s, 1H), 6.51 (s, 1H), 4.60 (t, J=6.2 Hz, 1H), 3.15 (br, 1H), 2.68 (s, 3H), 2.68 (m, 2H), 2.48 (q, J=7.3 Hz, 2H), 2.07 (s, 3H), 1.07 (t, J=7.3 Hz, 3H); $^{13}$C NMR (100.6 MHz, CDCl$_3$): δ212.0, 165.1, 153.3, 140.4, 118.1, 115.8, 72.9, 47.3, 37.0, 16.6, 14.8, 7.5; MS: 272 (MH$^+$), 294 (MNa$^+$).

Compound 15

[α]$_D$=−31.20° (c=2.5, CHCl$_3$); $^1$H NMR (400 MHz, CDCl$_3$): δ7.04 (s, 1H), 6.47 (s, 1H), 5.74 (m, 2H), 5.28 (t, J=6.7 Hz, 1H), 5.08 (d, J=17.1 Hz, 1H), 5.02 (d, J=10.2 Hz, 1H), 4.97 (d, J=17.2 Hz, 1H), 4.94 (s, 2H), 4.92 (d, J=10.3 Hz, 1H), 4.33 (m, 1H), 3.72 (dd, J=7.0, 2.2 Hz, 1H), 3.14 (m, 1H), 2.48 (m, 3H), 2.27 (dd, J=17.0, 6.1 Hz, 1H), 2.05 (s, 3H), 1.98 (m, 2H), 1.50–1.10 (m, 5H), 1.22 (s, 3H), 1.02 (s, 3H), 1.02 (d, J=6.8 Hz, 3H), 0.94 (s, 9H), 0.88 (s, 9H), 0.88 (d, J=6.8 Hz, 3H), 0.86 (s, 9H), 0.11 (s, 6H), 0.09 (s, 3H), 0.04 (s, 3H), 0.02 (s, 6H); $^{13}$C NMR (100.6 MHz, CDCl$_3$): δ217.7, 172.2, 171.1, 152.8, 138.9, 136.7, 133.4, 121.2, 117.8, 116.5, 114.4, 78.7, 77.6, 74.0, 63.2, 53.3, 45.2, 40.3, 38.8, 37.5, 34.3, 30.4, 27.0, 26.2, 26.0, 25.8, 23.2, 20.3, 18.5, 18.2, 17.6, 15.4, 14.5, −3.7, −3.8, −4.3, −4.7, −5.5; HRMS: (C$_{46}$H$_{85}$NO$_6$SSi$_3$Cs=996.4460) found 996.4494 (MCs$^{30}$).

Compound 12

[α]$_D$=−13.42° (c=0.37, CHCl$_3$); $^1$H NMR (400 MHz, CDCl$_3$): δ7.01 (s, 1H), 6.52 (s, 1H), 5.80 (m, 1H), 5.12 (d, J=17.4 Hz, 1H), 5.09 (d, J=11.3 Hz, 1H), 4.93 (s, 2H), 4.18 (t, J=6.7 Hz, 1H), 2.38 (m, 3H), 2.02 (s, 3H), 0.93 (s, 9H), 0.11 (s, 6H ); $^{13}$C NMR (100.6 MHz, CDCl$_3$): δ172.1, 153.0, 141.4, 134.6, 119.0, 117.8, 115.7, 76.4, 63.2, 40.0, 25.7, 18.2, 14.4, −5.5; MS: 340 (MH$^+$), 362 (MNa$^+$).

Compound 15

[α]$_D$=−43.7° (c=0.3, CHCl$_3$), Lit. −44.2° (c=0.6, CHCl$_3$).

Compound 16

[α]$_D$=−41.1° (c=0.3, CHCl$_3$); HRMS: (C$_{26}$H$_{40}$NO$_6$S= 494.2576) found 494.2582 (MH$^+$)

Compound 7

[α]$_D$=−71.6° (c=0.5, CHCl$_3$); $^1$H NMR (600 MHz, CDCl$_3$): δ6.95 (s, 1H), 6.60 (s, 1H), 5.38 (d, J=11.1 Hz, 1H), 5.20 (d, J=7.0 Hz, 1H), 4.17 (d, J=10.9 Hz, 1H), 3.47 (br s, 1H), 3.76 (s, 1H), 3.11 (m, 1H), 2.96 (br s, 1H), 2.89 (dd, J=14.3, 11.5 Hz, 1H), 2.68 (s, 3H), 2.48 (dd, J=15.0, 11.4 Hz, 1H), 2.37 (dd, J=15.0, 2.3 Hz, 1H), 2.17 (m, 1H), 2.08 (s, 3H), 1.72 (s, 3H), 1.57 (m, 1H), 1.33 (s, 3H), 1.17 (d, J=6.9 Hz, 3H), 1.09 (s, 3H), 0.99 (d, J=7.1 Hz, 3H); $^{13}$C NMR (150.9 MHz, CDCl$_3$): δ220.3, 170.6, 165.0, 152.0, 139.4, 129.9, 129.3, 119.3, 115.8, 76.7, 73.7, 72.5, 53.3, 42.0, 39.1, 38.1, 36.3, 32.5, 28.6, 28.1, 23.0, 22.8, 19.08, 19.04, 16.2, 15.7, 14.2, 13.5; HRMS: (C$_{27}$H$_{41}$NO$_5$SNa=514.2784) found 514.2589 (MNa$^+$).

Compound 27

[α]$_D$=−30.2° (c=0.5, CHCl$_3$); $^1$H NMR (600 MHz, CDCl$_3$): δ6.95 (s, 1H), 6.60 (s, 1H), 5.49 (dd, J=10.8, 1.1 Hz, 1H), 5.29 (m, 1H), 4.01 (dt, J=10.7, 2.5 Hz, 1H), 3.74 (br s, 1H), 3.19 (m, 1H), 3.13 (d, J=3.2 Hz, 1H), 2.69 (s, 3H), 2.53 (dd, J=14.9, 10.7 Hz, 1H), 2.45 (dd, J=14.7, 2.4 Hz, 1H), 2.44 (t, J=11.0 Hz, 1H), 2.32 (d, J=14.4 Hz, 1H), 2.30 (d, J=4.2 Hz, 1H), 2.20 (m, 1H), 2.08 (d, J=0.9 Hz, 3H), 1.87 (m, 1H), 1.82 (br s, 1H), 1.63 (m, 1H), 1.62 (s, 3H), 1.55 (m, 1H), 1.47 (m, 1H), 1.28 (s, 3H), 1.25 (m, 1H), 1.17 (d, J=6.8 Hz, 3H), 1.05 (s, 3H), 0.96 (d, J=7.0 Hz, 3H); $^{13}$C NMR (150.9 MHz, CDCl$_3$): δ219.7, 170.6, 164.9, 152.2, 137.7, 131.4, 128.8, 119.9, 116.3, 76.6, 76.3, 73.2, 60.4, 52.1, 44.3, 44.1, 38.4, 36.4, 29.3, 26.9, 22.0, 20.1, 19.2, 16.6, 15.8, 15.3; HRMS: (C$_{27}$H$_{42}$NO$_5$S=492.2784) found 492.2798 (MH$^+$).

What is claimed is:

1. A process for enantioselectively resolving a racemic mixture of an aldol synthon, the racemic mixture including a first and a second enantiomer of the aldol synthon, said process comprising the following steps:

Step A: Catalyzing a retro-aldol reaction for enantioselectively converting the first enantiomer of the aldol synthon to form an aldehyde product while leaving the second enantiomer of the aldol synthon unmodified, said catalysis employing a catalytic antibody selected from the group consisting of 84G3, 85H6, and 93F3; and then Step B: Separating the aldehyde product from the unmodified second aldol synthon.

2. A process according to claim 1 wherein the racemic mixture of the aldol synthon, the aldehyde product, the unmodified second enantiomer of the aldol synthon, and the retro-aldol reaction are all represented as follows:

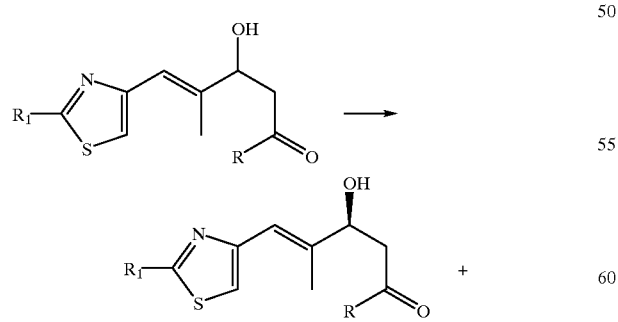

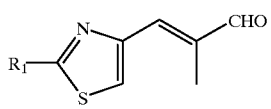

wherein R$_1$ is a radical selected from the group consisting of Me, CH$_2$OH, SMe, and OMe and R is a radical selected from the group consisting of Me, Et, n-Pr, n-Bu, n-Pentyl, and n-Bu-1-en-4-yl.

3. A process for enantioselectively resolving a racemic aldol synthon, the racemic aldol synthon including a first and a second enantiomer, said process comprising the following steps:

Step A: Catalyzing a retro-aldol reaction for enantioselectively converting the first enantiomer of the aldol synthon to form an aldehyde product while leaving the second enantiomer of the aldol synthon unmodified, said catalysis employing a catalytic antibody, the retro-aldol reaction being represented as follows:

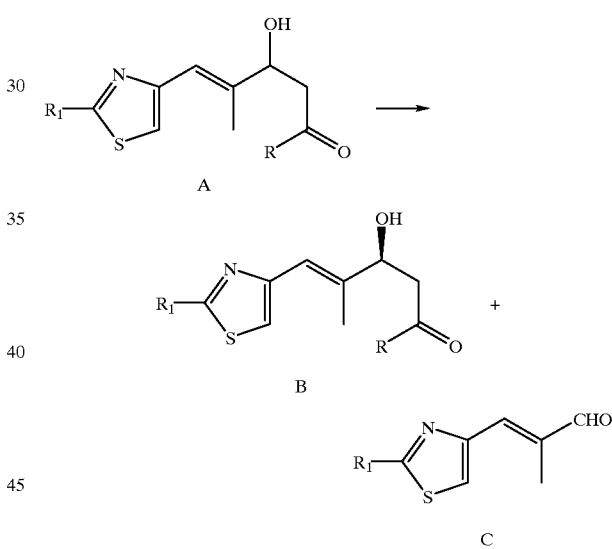

wherein A represents the the racemic aldol synthon, B represents the unmodified second enantiomer of the aldol synthon, and C represents the aldehyde product; wherein R$_1$ is a radical selected from the group consisting of Me, CH$_2$OH, SMe, and OMe and R is a radical selected from the group consisting of Me, Et, n-Pr, n-Bu, n-Pentyl, and n-Bu-1-en-4-yl; and then Step B: Separating the aldehyde product from the unmodified second aldol synthon.

* * * * *

UNITED STATES PATENT AND TRADEMARK OFFICE
CERTIFICATE OF CORRECTION

PATENT NO. : 6,294,374 B1
DATED : September 25, 2001
INVENTOR(S) : Sinha et al.

It is certified that error appears in the above-identified patent and that said Letters Patent is hereby corrected as shown below:

Column 1,
Line 4, insert -- This invention was made with government support under Contract No. CA 27498 by the National Institutes of Health. The government has certain rights in the invention. --

Signed and Sealed this

Ninth Day of April, 2002

Attest:

JAMES E. ROGAN
Attesting Officer
Director of the United States Patent and Trademark Office